United States Patent [19]

Kozam

[11] Patent Number: 4,575,375
[45] Date of Patent: Mar. 11, 1986

[54] PERIODONTAL POCKET IRRIGATING AND MEDICATION DELIVERY DISPENSER AND GEL SYSTEM

[76] Inventor: George Kozam, 234 E. Clinton Ave., Tenafly, N.J. 07670

[21] Appl. No.: 667,575

[22] Filed: Nov. 2, 1984

[51] Int. Cl.[4] .............................................. A61M 5/18
[52] U.S. Cl. ....................................... 604/185; 222/96
[58] Field of Search ........................ 604/185, 239, 212; 222/96

[56] References Cited

U.S. PATENT DOCUMENTS

| | | | |
|---|---|---|---|
| 881,469 | 3/1908 | Hale | 604/239 |
| 1,876,452 | 9/1932 | Gusdorf | 222/96 |
| 3,221,940 | 12/1965 | Watson, Jr. | 222/96 |
| 3,332,579 | 7/1967 | Peters | 222/96 |
| 4,019,655 | 4/1977 | Moeller | 222/96 |
| 4,258,864 | 3/1981 | Karamanolis et al. | 222/96 |

*Primary Examiner*—John D. Yasko
*Attorney, Agent, or Firm*—Edward F. Levy

[57] ABSTRACT

A periodontal pocket irrigating and treatment system includes a dispenser capable of containing a medication. The system enables an individual patient to self-administer a medication or irrigant into periodontal pockets while at home or travelling. A housing holds a tube of medication, and a roller squeezes the tube, thereby releasing an incremental portion of the medication therefrom. A control, operable from the outside of the housing, urges the roller in increments along the interior of the housing, squeezing the tube in a controlled fashion. A nozzle is attached to the tube for delivering the medication from the tube through a nozzle outlet end of small diameter to the periodontal pocket. Optionally, a flexible tip is attached to end of nozzle for elimination of pain and for guidance around curvatures of the periodontal pocket. A ratchet preferably controls the amount of medication dispensed by the device. The medication preferably is a gel, but may be in other form, which includes an active medication and a water-soluble carrying agent. In one embodiment, the active medication is contained in micropellets in the gel.

12 Claims, 5 Drawing Figures

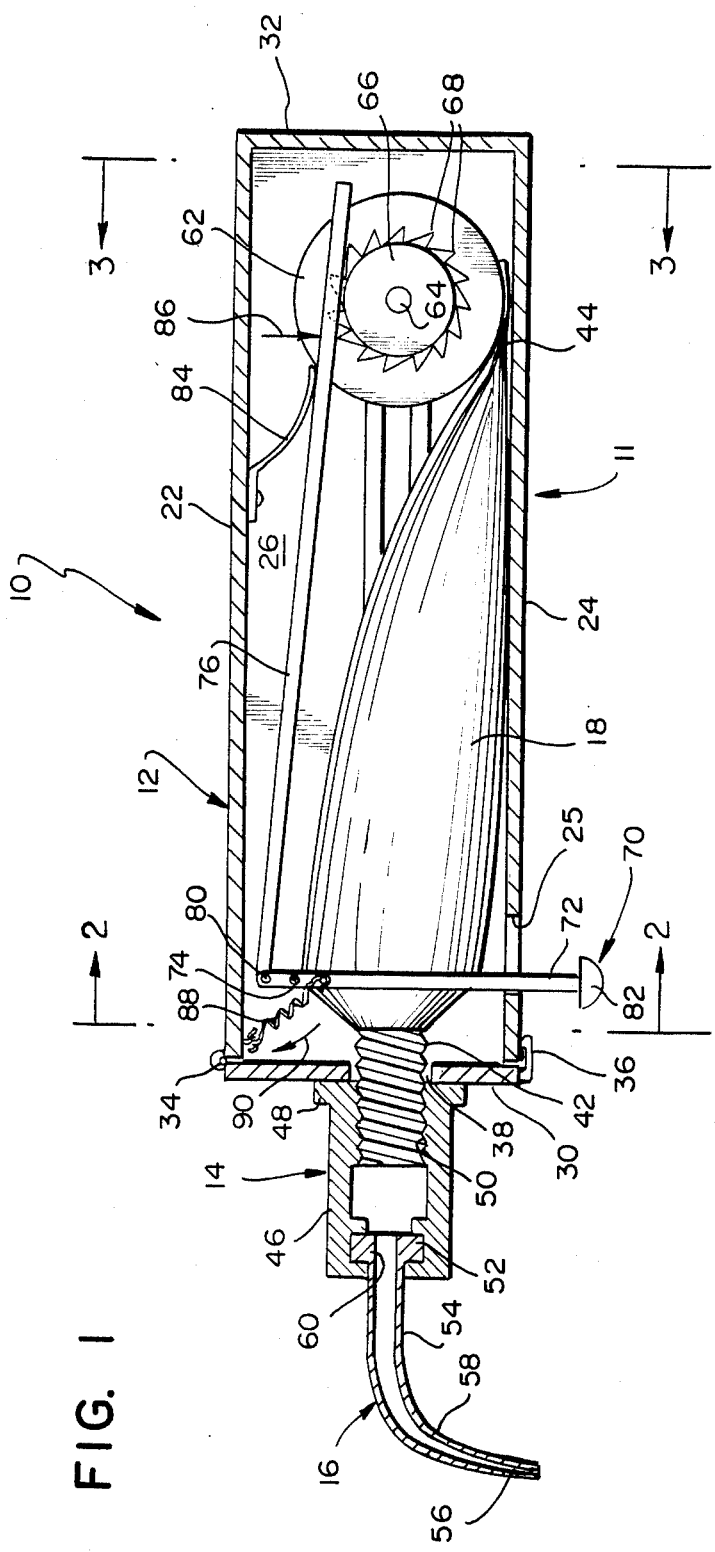
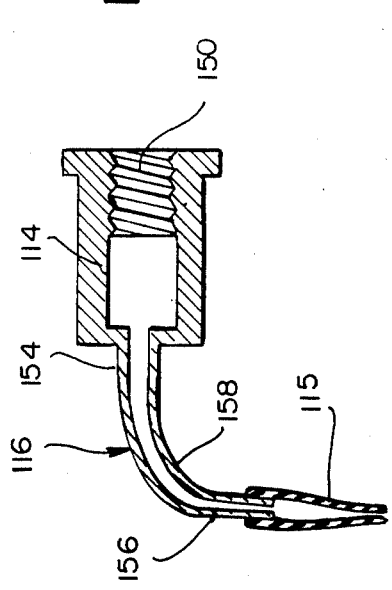
FIG. 1
FIG. 4

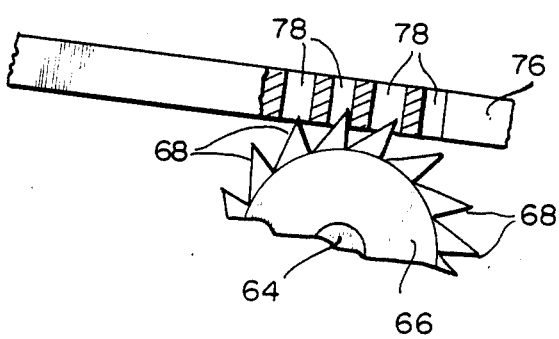
FIG. 1A
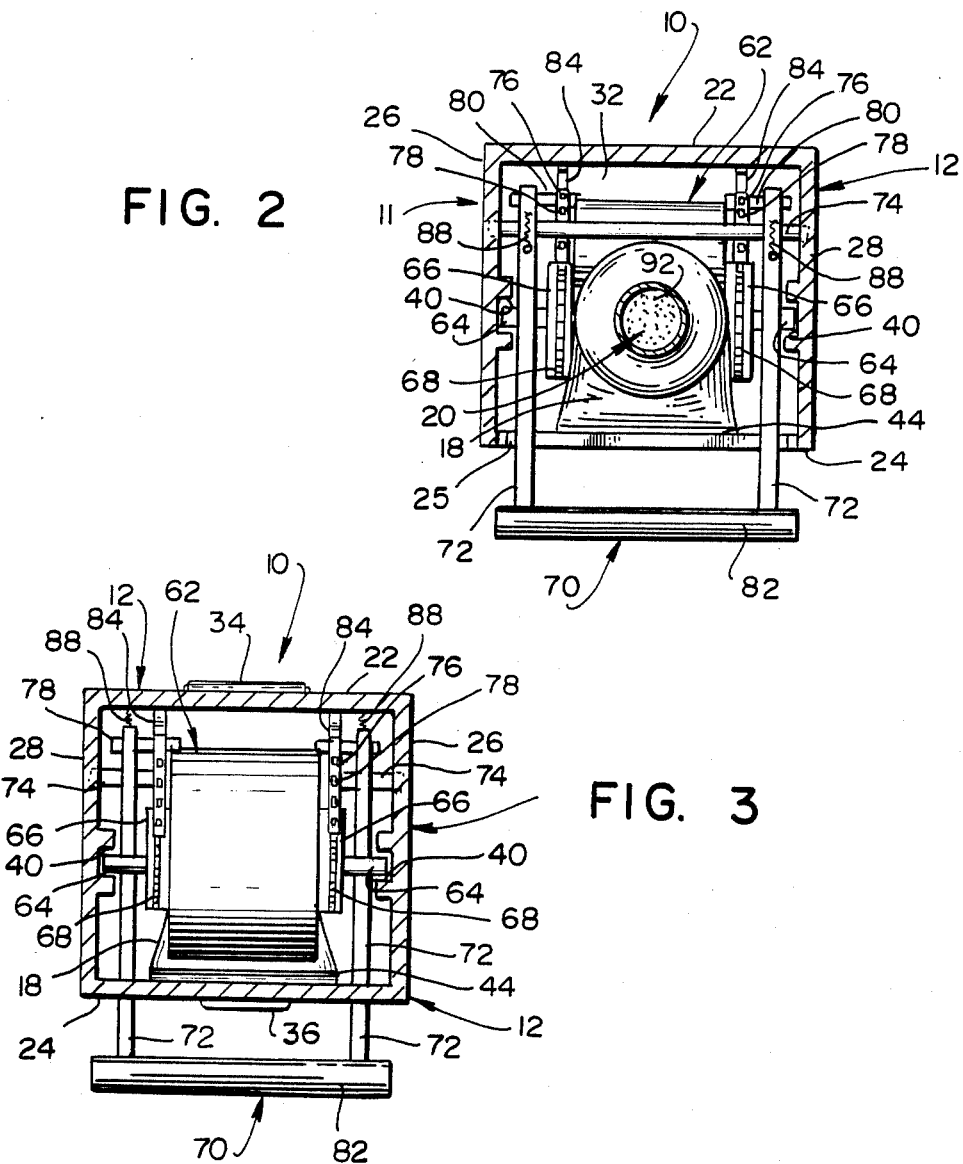
FIG. 2
FIG. 3

PERIODONTAL POCKET IRRIGATING AND MEDICATION DELIVERY DISPENSER AND GEL SYSTEM

BACKGROUND OF THE INVENTION

The present invention relates to a system devised for treating periodontal disease. More particularly, it relates to a hand-held dispenser device in the nature of a syringe which may be used by a lay person in his home or on his travels to conduct a course of antisepsis and maintenance treatment of that disease, as well as a multicomponent gel for use with such device.

Many people are afflicted with periodontal disease, i.e., gingivitis and periodontitis. The most common symptoms of periodontal disease are gingival and alveolar inflammation due to subgingival bacterial accummulations known as placque which cause deepening of the normal gingival crevice, leading to gum recession and deep gingival pockets. Bacterial inflammation is the main cause of these conditions. These pockets then retain more food and bacteria in their base, where the pathology develops, which pockets are not reachable for cleansing by ordinary means, and the trapped food debris becomes growth medium for bacteria. This then perpetuates the septic, inflammatory process and extends the pathology so that as pockets get deeper, the alvealar bone dissolves, pus extrudes, and the teeth become loose. This is a condition commonly known as pyorrhea.

The purpose of this dispenser-gel system is to introduce subgingivally antiseptic, anti-inflammatory, anti-placque and sedative medications to these inaccessible areas in a reliable, repeatable and convenient manner. Moreover, it is the function of the multi-purpose liquids, gels, emulsions or suspensions to carry these medications in a prolonged timed-release form and in consistencies which cannot be easily dislodged from the pockets by oral fluids so that their medicinal effects could last longer, perhaps as long as 12 to 24 hours. This would permit treatment applications once in 24 hours, yet maintain treatment effects throughout this time period.

The current methods of treatment fall into two catagories. In the first, periodontal surgery is used to shorten the depth of the pocket by cutting away part of the gum wall. This results in extreme thermal sensitivity of the denuded tooth roots and has only a small benefit in keeping pockets clean. The surgery is followed by curettage. However, even with this regular dental scraping, the debris and plaque deposits accummulate and the pockets progress deeper. The second method, namely non-surgical periodontics, involves the patient's making of a paste of sodium bicarbonate and hydrogen peroxide and, by supra-gingival toothbrush massage, attempting to work the paste into the pocket depth. This is rarely successful and is unreliable in that some pockets are not located in areas of the mouth which can be reached by a toothbrush, and even if the pockets can be reached, the material seldom if ever reaches to the bottom of pockets 6–12 mm. deep. In addition, since no pre-mixed product of this type is available on the market, the necessity for mixing of the paste adds to the inconvenience of the process and becomes a disincentive, which induces non-compliance by the patient and is counterproductive.

Additionally, some commercial pulsating devices, such as that sold under the trademark "Water-Pik", intended to dislodge food debris between teeth and massage the outer surface of the gums, are unsuitable for periodontal treatment because they apply excessive water pressure and may damage very tender intra-pocket tissues and do not induce antiseptic, anti-inflammatory and other treatment effects. Their effect in the periodontal pocket, if any, is extremely short lasting.

Thus, the patient is left without recourse to home therapy and must rely upon course after course of painful dental surgery and curettage and further progress of the disease.

Also lacking in the art is any commercially available medication which may be used by an individual as part of a course of home treatment of subgingival periodontal disease. The above-described combination of hydrogen peroxide and baking soda must be prepared by the patient, and may not last long. Anything which acts to discourage a patient from following the prescribed course of treatment, and the repeated mixing of the medication is a considerable disincentive to the patient's continuing to conduct the prescribed treatment and so should be avoided.

Accordingly, it is an object of the present invention to provide a device which overcomes the deficiencies of the prior art, and facilitates the home treatment of patients suffering from periodontal disease.

Another object of the invention is to provide a device which is capable of being conveniently hand-held, unlike a hypodermic syringe which requires the use of the thumb and two fingers. The device is also hand controlled, and is capable of dispensing predetermined portions of medication into periodontal pockets.

It is a further object of the invention to provide a multi-component medication in the form of a packaged, long active, timed-release gel, for use in home maintenance treatment of patients suffering from periodontal disease.

SUMMARY OF THE INVENTION

In accordance with the present invention, there is provided a periodontal pocket irrigating or treatment dispenser device for use with a tube capable of containing a medication, comprising a housing, means for retaining the tube within the housing, actuating means for squeezing the tube thereby causing the medication to be forced from the tube, and means for controlling the actuating means to control the amount of medication forced from the tube.

In a preferred embodiment of the invention, the actuating means includes a roller, the housing includes means for guiding the roller along a predetermined path in squeezing contact with the tube, and the means for controlling includes drive means for urging the roller along the path. The drive means includes at least one perforated bar or track pivotably disposed within the housing, and having a plurality of apertures therein, the roller having ratchet means for engaging the apertures, whereby to move the roller in predetermined increments so as to prevent overfeeding of the medication from the tube.

According to a feature of the invention, a narrow nozzle is attached to the tube for delivering the medication from the tube to the periodontal pocket. Optionally, a short, smooth flexible tube-like structure may be attached to the tip of the nozzle in order to be able to follow the curvatures of roots or pockets to the bottom of the periodontal pocket.

According to a another feature of the invention, there is provided a medication for use in the treatment of periodontal disease comprising a water-soluble carrying agent, an active medication in the water-soluble carrying agent, the active medicating ingredient being contained within micropellets, or within mixtures, emulsions, gels, suspensions or fluids having timed-release capabilities, and the water-soluble carrying agent including a preservative.

Additional objects and advantages of the invention will become apparent from the following description when taken in connection with the accompanying drawings, in which like reference numerals designate the same elements, and in which:

BRIEF DESCRIPTION OF THE DRAWINGS

FIG. 1 is a longitudinal cross section through a periodontal pocket irrigating system in accordance with the invention, shown at the beginning of its operative cycle;

FIG. 1A is an enlarged detail of a portion of FIG. 1, illustrating meshing between the roller of the inventive system and a portion of the actuator thereof;

FIG. 2 is a transverse cross-section through the front portion of the system as taken along the line 2—2 of FIG. 1;

FIG. 3 is a transverse cross-section through the rear portion of the system as taken along the line 3—3 of FIG. 1; and FIG. 4 is a sectional view illustrating an alternate embodiment of the nozzle used with the system of FIG. 1.

DESCRIPTION OF THE PREFERRED EMBODIMENTS

Referring in detail to the drawings, there is shown a periodontal pocket irrigating and treatment system made in accordance with the present invention and designated generally by reference numeral 10. It is here noted that FIGS. 1, 2, and 3 illustrate three different views of a preferred embodiment of system 10, while FIG. 1A is a detail of FIG. 1, and FIG. 4 shows an alternate embodiment of the nozzle portion of the system.

As shown in FIG. 1, system 10 includes a portable dispenser device 11 which comprises three separate elements: a housing 12, a coupling member 14 and a nozzle 16; and is adapted to contain a tube 18 or other flexible container such as a soft plastic bag, and to dispense therefrom a medication 20 (FIG. 2).

Housing 12 is preferably rectangular in shape, as shown, and includes a top wall 22, a bottom wall 24 having a slot 25 therein, left and right side walls 26 and 28 (FIGS. 2 and 3), a front wall 30 and a rear wall 32. A hinge 34 mounts the top end of front wall 30 to the forward end of top wall 22 so that the front wall 30 may be opened for removal and replacement of the tube 18. A latch 36 releasably secures front wall 30 in its closed position. Front wall 30 is formed with a circular aperture 38 therein. Each of the side walls 26 and 28 is formed with an elongated, longitudinally-extending guide slot 40 on its inner surface, as shown in FIGS. 2 and 3.

The tube 18, containing medication 20, is preferably a conventional squeezable tube similar to that used for containing toothpaste, for example, and is made of metal or plastic. The tube 18 terminates in the usual threaded cylindrical outlet end 42, which, in the mounted position of tube 18, projects through the housing front wall 30, as shown in FIG. 1. The tube 18 also has a flattened opposite end 44, as is conventional.

Coupling member 14 comprises a tubular cylindrical body 46 having a annular flange 48 at one end surrounding an internally-threaded opening 50. At its opposite end, the coupling member 14 is formed with an annular groove 52 sized to receive and mount the nozzle 16. In use of the dispenser device 11, the front wall 30 is unlatched and opened, and the tube 18 is inserted within the housing 12. The front wall 30 is then lowered toward its closed position and the threaded end 42 of tube 18 is fitted through the aperture 38 of front wall 30, so that said threaded end 42 projects outwardly of front wall 30. The front wall 30 is then latched in closed position, and the projecting portion of the tube threaded end 42 is grasped and pulled further outwardly through aperture 38. The coupling member body 46 is now screwed upon the threaded end 42 of tube 18 by means of its internal threading 50, and is turned thereon until its flange 48 abuts the outer surface of front wall 30, in the manner shown in FIG. 1. The tube 18 is thereby fixedly mounted within the housing 12.

The nozzle 16, in the embodiment of FIG. 1, is removable from the coupling member 14 so that it may be replaced after use. For this purpose the nozzle 16 is made of rubber or other flexible material, having a wide inlet portion 54 at one end thereof and a narrow outlet portion 56 at the opposite end thereof, connected by an angular bend 58 which may be a right angle bend. The wide inlet portion 54 terminates in an annular flange or tongue 60.

The nozzle 16 is attached to the coupling member 14 by snap-fitting the flexible flange or tongue 60 within the annular groove 52 of the coupling member body 46. When the tube 18 is now compressed, its gel content will be forced therefrom through the coupling member 14 and the connected nozzle 16, and into the periodontal pocket in which the nozzle is inserted.

The dispenser device 11 also includes manually operable actuating means for compressing the flexible tube 18 so as to feed the contained medication therefrom through the nozzle 16 in a controlled manner. Said actuating means includes a cylindrical roller 62 mounted on a central shaft 64 which extends at each end within the respective elongated guide slots 40 of the housing side walls 26 and 28, as shown in FIGS. 2 and 3. Affixed to each side of the roller 62 is a respective ratchet wheel 66 having angular teeth 68. The roller 62 may be molded from plastic with the ratchet wheels 66 and shaft 64 formed integrally therewith.

The actuating means further comprises an actuator assembly 70, which includes a pair of elongated levers 72, one disposed proximate to left side wall 26 and the other proximate to right side wall 28, as shown in FIG. 2. Each lever 72 is pivotably mounted intermediate its ends upon a pivot rod 74 extending between left and right side walls 26 and 28 and fixed thereto. The actuator assembly 70 also includes a pair of opposed perforated bars or tracks 76, each having a row of apertures 78 therein, as best seen in FIG. 1a. Each perforated bar or track 76 is pivotably connected at its forward end to the upper end of a respective lever 72 by means of a pivot pin 80 located above the pivot rod 74. Neither pivot pin 80 is fixed with respect to housing 12, but both are movable about pivot rod 74, because each pivot pin 80 is mounted on a respective lever 72, which is in turn freely pivotable about pivot rod 74. Both levers 72 extend through the slots 25 in the bottom wall 24 of housing 12 and project below said bottom wall. The projecting ends of levers 72 are interconnected by an elongated finger piece 82 for actuation by the user in a manner to be presently explained.

The combination of the ratchet wheels 66 of roller 62 and perforated bars 76 of actuator assembly 70 acts as a ratchet. Any other configuration of elements which provides ratcheting action of roller 62 is considered to be within the scope of the invention.

Actuator assembly 70 further includes at least one leaf spring 84 mounted at one end thereof on the housing top wall 22, with its other end engaging the upper surface of a respective perforated bar 76. Each leaf spring 84 is arranged to bias the respective perforated bar or track 76 in the downward direction indicated by the arrow 86 in FIG. 1 so as to urge the perforations 78 into engagement with the teeth 68 of ratchet wheel 66. The actuator assembly 70 also includes a coil spring 88 attached at one end thereof to the lower arm of lever 72 beneath the pivot rod 74. The coil spring 88 is arranged to bias the lower arm of lever 72 in the direction of arrow 90 in FIG. 1, so that said arm is normally urged into abutment with the forward end of slot 25, in the position shown in FIG. 1.

As previously stated, dispenser device 11 is used with tube 11 containing medication 20 therein (FIG. 2). It is preferred that the active ingredients of medication 20 be contained within a plurality of micropellets 92. Medication 20 may also be in the form of a gel or paste, or mixtures of gels, emulsions, suspensions or fluids, but may be in any form which is capable of being dispensed from tube 18 through nozzle 16. It is preferred that the gel which comprises medication 20 be capable of use by a patient at home, and so should preferably have certain characteristics conducive to such a use.

Specifically, the viscosity of medication 20 must be sufficiently high to permit it to flow from tube 18 in a controlled manner when roller 62 squeezes tube 18, rather than to seep therefrom in an uncontrolled fashion. The viscosity must be low enough to permit medication 20 to be conveniently dispensed by device 11, without the necessity of exerting an excessive amount of force. In the preferred embodiment, at a temperature of approximately 37 degrees Centigrade (i.e. approximately body temperature), a viscosity of medication 20 of from about 30 to about 800 centipoise is satisfactory, and a viscosity of from about 200 to about 400 is preferred.

Another important physical characteristic of medication 20 is that it contains an active medicating ingredient. This active ingredient is prescribed by the treating dentist, and is preferably contained within micropellets 92 or a mixture of gels, emulsions, pastes or fluids of varying solubility, to preserve the efficacy of the medication, and allow the time-release thereof. The active ingredient, however, must be carried in a carrying agent for purposes of dispensing medication 20. The primary characteristic of the carrying agent is that it be water-soluble, so that, once dispensed into the depth of the desired periodontal pocket, it slowly disolves and thereby releases the medication contained therein.

Since water-soluble carrying agents may tend to deteriorate upon exposure to the air, it is also preferred that medication 20 contain a preservative appropriate for a water-soluble material, such as, for example, chlorhexadine.

To use dispenser device 11, the patient grips housing 12 with one hand and positions it so that his or her thumb grips finger piece 82. In this position, movement of the patient's thumb rearwardly, or in a right-hand direction as viewed in FIG. 1, will cause levers 72 to pivot about pivot rod 74. Once dispenser device 11 is securely gripped, it is positioned so that nozzle outlet portion 56 directs medication 20 passing therethrough into the desired periodontal pocket.

Once outlet portion 56 is in its desired position, dispenser device 11 is actuated to dispense medication 20 from tube 18. To commence this actuation, finger piece 82 of actuator assembly 70 is displaced by thumb pressure towards the rear of housing 12, causing the lower ends of levers 72 to pivot about pivot rod 74 in a counter-clockwise direction toward rear wall 32. This movement causes the upper ends of levers 72 to move in the opposite direction, thus pulling the perforated bars 76 toward the front wall 30. Because the perforated bars 76 are held by spring 84 in overlying relationship with the ratchet wheels 66, such movement of bars 76 initiates a ratcheting effect with ratchet wheel teeth 68, thereby causing roller 62 to rotate and travel towards front wall 30. Since rear end 44 of tube 18 is disposed beneath roller 62, the forward movement of roller 62 causes it to travel along tube 18, thereby squeezing tube 18 and causing medication 20 to exit therefrom into coupling member 14.

The continued movement of roller 62 causes more and more medication 20 to enter coupling member 14 which eventually fills up, and medication 20 flows into and through nozzle 16 until it fills outlet portion 56 thereof. After reaching outlet portion 56, medication 20 exits therefrom and into the desired periodontal pocket. Since, as shown, outlet portion 85 is relatively narrow, it may be readily inserted into a periodontal pocket between a tooth and the surrounding gum, and the passage of medication 20 therethrough may be accomplished with the controlled expenditure of relatively little force.

The progressive narrowing of the cross-section of the channel through which medication 20 passes imparts increasing pressure thereto. This pressure, however, may be readily controlled, by the strength with which finger piece 82 is pulled back. Thus, dispenser device 11 dispenses medication 20 with the amount of force desired, and prevents the introduction of excessively pressured medication 20 into the sensitive periodontal pockets.

Additionally, the amount of medication 20 which is dispensed by dispenser device 11 is controlled by virtue of the ratcheting action of actuator assembly 70. This ratcheting action requires that dispenser device 11 be reset after perforated bar 76 has moved the maximum distance permitted by the construction of dispenser device 11. It will be seen in FIG. 1 that the movement of levers 72 is limited by the length of slot 25, which length is such that the perforated bar 76 will cause the roller 62 to rotate and move forward only by a distance equal to the size of two or three teeth 68 of the ratchet wheel 66. When the roller has moved its maximum distance, finger piece 82 is released, thereby allowing coil spring 88 to pull levers 72 back into their rest positions, in the direction indicated by the arrow 90. This movement causes perforated bars 76 to move towards rear wall 32, and disengage apertures 78 from teeth 68. These elements are re-engaged by the action of leaf spring 84, which biases perforated bar 76 into contact with teeth 68, and thus the ratcheting action of actuator assembly 70 causes the unidirectional movement of roller 62 along the length of housing 12, so that the continued use of dispenser device 11 allows the gradual dispensing of medication 20 through nozzle outlet portion 56 in small increments and in a carefully controlled fashion. Since the vertical movement of roller 62 is constrained by guides 40, as described, the movement of roller 62 along housing 12 causes the gradual squeezing of tube 18, and thus the appropriate dispensing thereof through outlet portion 56.

FIG. 4 illustrates an alternate embodiment of nozzle and coupling member which, in this instance, are formed integrally with each other. The nozzle 114 and coupling member 116 are molded as a single unit from a plastic which is more rigid than the rubber or soft plastic which constitutes the nozzle 16 of FIG. 1. The coupling member 114 has essentially the same construction as the coupling member 14 and is sized to be mounted upon the dispenser device 11 of FIG. 1 by screw attachment of its internal threading 150 to the threaded end of the contained tube 18. The nozzle 116 is also generally similar to the nozzle 16 of FIG. 1, having a wide inlet portion 154 joined to a narrow outlet portion 156 at an angular bend 158. In this instance, however, the narrow outlet portion 156 is not inserted directly into the periodontal pocket of the patient because of its rigidity. Rather, a flexible tip 115, preferably of rubber, is mounted on the end of nozzle outlet portion 156 to facilitate entry to the bottom of the periodontal pocket. The tip 115 is made narrow and thin-walled so that it is very flexible and is capable of following the curvatures of roots or of walls of the pocket to the very bottom of the periodontal pocket without causing pain or irritation. The tip 115 is mounted frictionally, or by a compressive band, on the mouth of the nozzle outlet portion 156 and may be removed when desired for replacement.

Although the invention is described as a dispenser device 11 which expresses medication from a tube 18, one embodiment of the invention contemplates the use of tube 18 and nozzle 16 or nozzle 116 without the use of dispenser device 11. In this embodiment, the recited formulation of medication 20 has its viscosity adjusted to permit squeezing from tube 18 without the need for the mechanical advantage provided by dispenser device 11.

Having described specific preferred embodiments of the invention with reference to the accompanying drawings, it is to be understood that the invention is not limited to those precise embodiments and that various changes and modifications may be effected therein by one skilled in the art without departing from the scope or spirit of the invention as defined in the appended claims.

What is claimed is:

1. A periodontal pocket irrigating and treatment dispenser for use with a tube capable of containing a medication comprising:
a housing;
means for retaining said tube within said housing;
actuating means including a roller for squeezing said tube, to force the contained medication therefrom; and means
means for controlling said actuating means to control the amount, speed and force of medication squeezed from said tube,
said means for controlling including at least one perforated bar movably disposed within said housing, and said roller including ratchet means engaging said bar for movement of said roller with said bar in a direction in which said roller engages and squeezes said tube sufficiently to force said medication from said tube.

2. A periodontal pocket irrigating and treatment dispenser according to claim 1 which also includes guide means for guiding said roller in a longitudinal path along said tube as said roller is moved by said perforated bar.

3. A periodontal pocket irrigating and treatment dispenser according to claim 1 wherein said means for controlling also includes means for biasing said bar toward said ratchet means.

4. A periodontal pocket irrigating and treatment dispenser according to claim 1 wherein said tube includes threads at one end thereof, and said means for retaining includes means for engaging said threads.

5. A periodontal pocket irrigating and treatment dispenser according to claim 4 further comprising a nozzle having a first end attachable to said tube to receive said medication therefrom, and a second end having means for guiding said medication into said periodontal pockets.

6. A periodontal pocket irrigating and treatment dispenser according to claim 4 which also includes a flexible tip attached to the mouth of the second end of said nozzle, said tip being sized for insertion into said periodontal pockets and being sufficiently flexible to follow the contour of said pockets and the tooth roots therein.

7. A periodontal pocket irrigating and treatment system comprising:
a flexible container containing medication of selected viscosity for treating periodontitis and having an outlet portion;
a housing sized to receive said container therein, said housing having an aperture through which said outlet portion projects;
said housing also including a longitudinal axis substantially aligned with said aperture;
said flexible container lying within said housing substantially along said longitudinal axis;
an elongated nozzle having a wide inlet end portion and a narrow outlet end portion connected by an angular bend;
coupling means for connecting the inlet end portion of said nozzle to the outlet portion of said container with said inlet end portion substantially aligned with the longitudinal axis of said housing and said outlet end portion extending substantially perpendicularly to said longitudinal axis;
said outlet end portion of said nozzle being tapered and being sized for insertion into said periodontal pocket; and
manually operable means for selectively compressing said flexible container sufficiently to force said medication therefrom through said nozzle.

8. A periodontal pocket irrigating and treatment system according to claim 4 in which said outlet end portion of said nozzle includes flexible means for guiding said medication into said periodontal pocket.

9. A periodontal pocket irrigating and treatment system according to claim 7 in which said compressing means includes a member movably mounted in said housing and an actuating member mounted on said housing and operatively connected to said member for moving said member in a direction to compress said flexible container, said actuating member being accessible from the exterior of said housing for manual operation.

10. A periodontal pocket irrigating and treatment system according to claim 7 in which said medication includes a viscous water-soluble carrying agent and an active medication ingredient.

11. A periodontal pocket irrigating and treatment system according to claim 10 wherein said water-soluble carrying agent has a viscosity of from about 30 to about 9000 centipoise at a temperature of about 37 degrees Centigrade.

12. A periodontal pocket irrigating and treatment system according to claim 10 wherein said active medication ingredient is contained within a plurality of time release micropellets embedded in said carrying agent.

* * * * *